United States Patent [19]

Vanderspurt

[11] 4,096,193

[45] Jun. 20, 1978

[54] PRODUCTION OF ALPHA BETA OLEFINICALLY UNSATURATED ALCOHOLS

[75] Inventor: Thomas H. Vanderspurt, Gillette, N.J.

[73] Assignee: Celanese Corporation, New York, N.Y.

[21] Appl. No.: 710,947

[22] Filed: Aug. 2, 1976

[51] Int. Cl.² .............................................. C07C 29/14
[52] U.S. Cl. .................................... 568/881; 252/475
[58] Field of Search ...................................... 260/638 B

[56] References Cited

U.S. PATENT DOCUMENTS 2,763,696   9/1956   Finch et al. ...................... 260/638 B Primary Examiner—Joseph E. Evans

[57] ABSTRACT

This invention provides an improved hydrogenation process for converting $\alpha,\beta$-olefinically unsaturated carbonylic compounds into the corresponding allylic alcohol derivatives in the presence of a novel silver-cadmium alloy catalyst. Acrolein is hydrogenated to allyl alcohol with 100 percent conversion and 70 percent yield.

10 Claims, No Drawings

PRODUCTION OF ALPHA BETA OLEFINICALLY UNSATURATED ALCOHOLS

BACKGROUND OF THE INVENTION

Several methods are known in the prior art for converting $\alpha,\beta$-olefinically unsaturated carbonylic compounds into the corresponding $\alpha,\beta$-olefinically unsaturated alcohols.

British Pat. No. 734,247 and U.S. Pat. No. 2,763,696 disclose a process whereby acrolein may be converted to allyl alcohol by means of a vapor phase hydrogenation process. According to this process, moderate yields of allyl alcohol are obtained when acrolein is treated with free hydrogen in the vapor phase at a temperature between 210° and 240° C in the presence of a catalyst comprising cadmium and one or more heavy metals of groups I, II, VI and VIII of the periodic table. Relatively high pressures are employed in the process on the order of 20 to 50 kilograms per square centimeter.

German Pat. No. 858,247 discloses a somewhat different process which is also useful for the conversion of acrolein to allyl alcohol. According to the German patent, good yields of allyl alcohol are obtained by reacting acrolein with free hydrogen in the presence of a catalyst containing cadmium oxide and a metal hydrogenating component which is preferably copper. The patent teaches that the best results are obtained when the process is operated at high temperatures and at high pressures on the order of 100–300 atmospheres.

It is also known to convert $\alpha,\beta$-unsaturated aldehydes into the corresponding unsaturated alcohols in the liquid phase by means of hydrogenation in the presence of a mixture of a copper soap and a cadmium soap. It is assumed that the copper salt is the catalyst and that the cadmium salt only serves the function of preventing the copper salt from being reduced to metallic copper. The use of a solution of a mixture of a copper salt and a cadmium salt for catalyst has the disadvantage that the system is extremely unstable under the required processing conditions, and fluctuations in conditions can cause reduction of the $Cd^{2+}$ salt and/or the $Cu^{2+}$ salt to metals.

U.S. Pat. No. 3,686,333 describes a liquid phase hydrogenation process for converting alkenals into alkenols in the presence of a catalyst mixture of a cadmium salt of a fatty acid and a transition metal salt of a fatty acid.

Japanese Patent No. 73-01,361 discloses a process for hydrogenating $\alpha,\beta$-olefinically unsaturated aldehydes into the corresponding allylic alcohol derivatives. The efficiency of the process is improved by the recycle of by-products to the hydrogenation zone, or by passage of the by-products stream into a second hydrogenation zone. The preferred catalysts are mixtures of cadmium and copper, cadmium and silver, cadmium and zinc, cadmium and chromium, copper and chromium, and the like. The Japanese patent states that under steady state conditions 1.5 moles/hour of acrolein are converted to 1.05 moles/hour of allyl alcohol and 0.4 mole/hour of n-propanol.

There remains a need for a commercially feasible vapor phase process for converting $\alpha,\beta$-olefinically unsaturated carbonylic compounds into allylic derivatives in higher efficiency and yield then has been achieved heretofore in the prior art.

Accordingly, it is an object of the present invention to provide an improved process for producing allylic alcohol derivatives by hydrogenation of $\alpha,\beta$-olefinically unsaturated carbonylic compounds.

It is another object of the present invention to provide a process for converting acrolein into allyl alcohol with a conversion of at least 95 percent and a yield of at least 70 percent.

It is further object of the present invention to provide a novel silver-cadmium alloy catalyst for selective hydrogenation of $\alpha,\beta$-olefinically unsaturated carbonylic compound to the corresponding allylic alcohol derivatives.

Other objects and advantages of the present invention shall become apparent from the following description and examples.

DESCRIPTION OF THE INVENTION

One or more objects of the present invention are accomplished by the provision of an improved hydrogenation process for converting an $\alpha,\beta$-olefinically unsaturated carbonylic compound into the corresponding allylic alcohol derivative which comprises reacting an $\alpha,\beta$-olefinically unsaturated carbonylic compound with hydrogen in the vapor phase at a temperature between about 0° and 300° C and a pressure between about 15 and 15000 psi in the presence of a catalyst comprising a silver-cadmium alloy on a carrier substrate, wherein the atomic ratio of silver to cadmium in the alloy is in the range between about 0.1 and 3.0 to 1.

The $\alpha,\beta$-olefinically unsaturated carbonylic compounds amenable to the presence invention process include those which correspond to the formula:

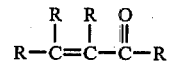

wherein R is a substituent selected from hydrogen and hydrocarbon radicals containing between one and about 10 carbon atoms. A preferred class of $\alpha,\beta$-olefinically unsaturated compounds corresponding to the above formula are those in which R is a substituent selected from hydrogen and alkyl groups containing between one and about four carbon atoms.

Illustrative of $\alpha,\beta$-olefinically unsaturated compounds which can be selectively hydrogenated in accordance with the invention process are acrolein, methacrolein, crotonaldehyde, tiglic aldehyde, $\alpha$-ethylacrolein, cinnamaldehyde, 2-hexenal, methylvinyl ketone, methylisopropenyl ketone, ethylvinyl ketone, cyclohexenylisopropenyl ketone, and the like. Heteroatoms such as halogen and nitrogen may also be present in the compounds being selectively hydrogenated to allylic derivatives.

In the practice of the invention process, the $\alpha,\beta$-olefinically unsaturated carbonylic compound and hydrogen at elevated temperature and pressure are passed in vapor phase through a reaction zone containing a novel silver-cadmium alloy catalyst having exceptional selective hydrogenation activity.

The reaction temperature of the hydrogenation process can vary in the range between about 0° and 300° C, and preferably between about 75° and 250° C, and most preferably between about 100° and 215° C.

The pressure of the hydrogenation process can vary in the range between about 15 and 15,000 psi, and preferably between about 75 and 5000 psi, and most preferably between about 250 and 2500 psi.

The mole ratio of hydrogen to α,β-olefinically unsaturated carbonylic compound in the vapor phase feed stream can vary in the range between about 1:1 and 100:1. For the selective hydrogenation of an aldehydic compound such as acrolein, the preferred mole ratio of hydrogen to carbonylic compound in the feed stream is in the range between about 5:1 and 200:1, and the most preferred mole ratio in the range between about 10:1 and 150:1.

The rate at which the vapor phase gas stream is contacted with the silver-cadmium alloy catalyst is not critical, and can be varied consonant with the other processing conditions to achieve an optimal balance of conversion and yield parameters. The flow rate of feed gas reactants can vary over a broad range between about a total of 10 moles and 1000 moles of feed gas reactants per liter of catalyst per hour. In the case of acrolein and methylvinyl ketone and other low molecular weight carbonylic compounds, a preferred flow rate of feed gas reactants is one which provides a catalyst contact time between about 0.1 and 50 seconds. By the invention process, acrolein can be converted to allyl alcohol with a space-time yield of greater than 900 grams per liter of catalyst per hour.

The process can be conducted either by passing the feed mixture through a fixed catalyst bed, or through a reactor wherein the catalyst is present in finely divided form and is maintained in a fluidized state by the upward passage there through of the gaseous reactants. The process is most conveniently carried out in a continuous manner, although intermittent types of operation can be employed. In a preferred method of continuous operation, the components of the feed stream are brought together and under the desired pressure are passed in vapor phase through the catalyst heated to the desired temperature. The reaction zone advantageously is an elongated tube or tubes containing the catalyst. The feed can be brought into contact with the catalyst in either the unheated or preheated condition. The effluent from the reactor can then be separated into its various constituents by conventional means, the most convenient of which is of fractional distillation. If desired, any unconverted portion of the carbonylic reactant present in the effluent can be recirculated through the catalyst in the reactor, preferably admixed with fresh feed gases.

CATALYST PREPARATION

The present invention also provides a novel catalyst composition which consists essentially of a silver-cadmium alloy on a carrier substrate, wherein the atomic ratio of silver to cadmium in the alloy is in the range of between about 0.1 and 3 to 1.

The carrier substrate can be selected from silica, Celite, diatomaceous earth, Kieselguhr, alumina, silica-alumina, titanium oxide, pumice, carborundum, boria, and the like. It is highly preferred that the silver-cadmium alloy be supported on a silica and/or alumina carrier substrate. The quantity of carrier substrate in the catalyst composition can vary in the range of between about 5 and 99.5 weight percent, based on the total catalyst weight.

The preferred catalysts are prepared by coprecipitating hydroxides of silver and cadmium from an aqueous solution of calculated quantities of water-soluble salts of silver and cadmium. The precipitation is effected by the addition of caustic to the aqueous solution. Preferably, the finely divided carrier substrate mass is slurried in the said aqueous medium immediately after the silver-cadmium hydroxides are precipitated. Finely divided porous materials such as fumed silica or diatomaceous earth are highly preferred carrier substrate materials for the preparation of the present invention catalysts.

After the coprecipitaition of silver-cadmium hydroxides has been accomplished, the solids phase is recovered by filtration or other conventional means. The filtered solids are washed with chlorine-free water until essentially neutral. For the purposes of a fixed bed operation, the dried filter cake preparation is calcined at a temperature between about 175° and 300° C for a period of about two to twenty hours or longer, and then the calcined material is ground and pelleted. Prior to use the catalyst pellets can be reduced in a stream of hydrogen at a temperature between about 50° and 250° C for a period of time up to about five hours. For a fluidized bed operation, the calcined catalyst preparation can be ground and sized in a conventional manner to satisfy process design requirements. The reduction of the catalyst can also be accomplished in situ during a vapor phase hydrogenation process.

There are several critical aspects of catalyst preparation which must be respected in order to achieve a novel type of hydrogenation catalyst having unique and advantageous properties in comparison to prior art catalysts for selective hydrogenation of acrolein type compounds to allyl alcohol type compounds.

Firstly, the silver-cadmium alloy in the catalyst must contain an atomic ratio of silver to cadmium in the range between about 0.1 and 3 to 1, and preferably between about 0.4 and 2.2 to 1.

Secondly, the silver and cadmium in the catalyst must be in the free metal state, and must be substantially in the form of an alloy, i.e., X-ray diffraction spectra should confirm the absence of unalloyed silver or cadmium crystals. Perferred silver-cadmium alloy catalysts are solid solutions which nominally exhibit an X-ray diffraction pattern which is substantially free of detectable unalloyed metal crystallite lines.

In terms of X-ray diffraction data as more fully described herein below, a preferred silver-cadmium alloy catalyst can consist substantially of α-phase silver-cadmium, without detectable splitting of X-ray diffraction lines which is indicative of silver-rich and/or cadmium-rich α-phase crystallites. Silver-cadmium catalysts which also have outstanding selectivity for high yield conversion of acrolein-type compounds into allyl alcohol-type compounds are those in which the alloy composition consists of more than about 50 percent of γ-phase silver-cadmium crystallites as characterized by X-ray diffraction pattern.

Thirdly, it has been found that the production of silver-cadmium alloy catalysts, which exhibit the greatest selectivity for converting acrolein to allyl alcohol, can be achieved if the coprecipitation step of the catalyst preparation is conducted within restricted limitations and under controlled conditions. Thus, the total concentration of the water-soluble salts (e.g., nitrate salts) in the aqueous solution should be maintained in the range between about 5 weight percent, and the solubility limit of the salts, and the quantity of caustic added as a precipitating agent should approximate the stoichiometric amount within narrow limits. It is particularly advantageous to employ a water-soluble hydroxide (e.g., an alkali metal hydroxide) as the caustic precipitating agent, and to add the caustic rapidly with stirring to facilitate formation of a precipitate of fine crystals. Excellent results are obtained, for example, if 17 grams of silver nitrate and 34 grams of cadmium nitrate are dissolved in 200 milliliters of water, and 18 grams of potassium hydroxide are dissolved in 200 milliliters of water, and both solutions are added simultaneously to 100 milliliters of water with rapid stirring.

Other precautions must be observed during catalyst preparation if highly selective silver-cadmium alloy compositions are to be achieved. It has been found that the calcination step of the catalyst preparation most advantageously must be conducted within narrowly controlled limitations. The calcination step should be accomplished at a temperature between about 175° and 300° C, and most preferably at a temperature between about 200° and 250° C. If calcination of a silver-cadmium alloy catalyst is conducted at a temperature above about 300° C, the resultant catalyst exhibits less selectivity for high yield conversion of acrolein to allyl alcohol in a vapor phase process.

The importance of controlled calcination conditions is apparent from a comparison of the data presented in the Examples hereinbelow with the data reported in Example VII of U.S. Pat. No. 2,763,696. In the said patent Example VII, over a silver-cadmium catalyst acrolein is hydrogenated in vapor phase to allyl alcohol in a yield of 38.3% at a conversion rate of 95%. This is in contrast to the results reported hereinbelow. In Example I, inter alia, acrolein is converted to allyl alcohol in yields above 70% at a conversion rate above 95%. The low selectivity of the U.S. Pat. No. 2,763,696 catalyst is believed to be attributable to the presence of a substantial quantity of unalloyed silver crystallites. The patent catalyst is calcined at 400° C for 2–6 hours during the preparation procedure. High calcination temperatures can have the effect of segregating the active metal species into large crystallites of unalloyed silver and unalloyed cadmium. The presence of unalloyed silver and/or cadmium is detrimental to the hydrogenation selectivity properties of silver-cadmium catalysts.

It has also been found that the silver-cadmium alloy catalysts of the present invention are most effective when supported on a carrier substrate, i.e., in combination with an internal diluent. Catalysts prepared without a carrier substrate have been found to have a lower activity and shorter catalyst life than the corresponding supported catalysts in vapor phase hydrogenation processes. A typical carrier substrate will have an initial surface area of more than about 1–10 $m^2/gm$, and an average pore diameter greater than about 20 A. A high proportion of small pores is detrimental to catalyst activity, if the size of the pores are such that capillary condensation of an acrolein-type compound occurs and causes pore blockage. This results in loss of catalytic activity.

The novel silver-cadmium alloy catalyst and X-ray diffraction characterization are more fully described in copending patent application Ser. No. 714,201 filed Aug. 13, 1976, incorporated herein by reference.

The following examples are further illustrative of the present invention. The reactions and other specific ingredients are presented as being typical, and various modifications can be derived in view of the foregoing disclosure within the scope of the invention.

EXAMPLE I

A catalyst was prepared by the rapid dropwise coaddition of 100 milliliters of a 1.0 molar $AgNO_3$, 0.49 molar $Cd(NO_3)_2$ solution and 100 milliliters of a 1.72 KOH solution to 400 milliliters of vigorously stirred doubly distilled water. About 19 grams of Cab-O-Sil H-5 silica (325 $m^2/g$, Cabot Corp. Boston, Mass.) were then thoroughly mixed with the resultant slurry of silver-cadmium coprecipitate. The slurry was filtered, and the filter cake was washed with about 600 milliliters of doubly distilled water. The filter cake was calcined in air at 250° C for 16 hours. The resultant material was crushed and screened to yield a 50!4 80 mesh fraction. Bulk chemical analysis of this material indicated that it containid 54% $SiO_2$, 17.3% Cd, 27.5% Ag with 0.3% K also present. Powder X-ray diffraction studies revealed that the composition contained metallic silver crystallites and cadmium oxyhydroxide $Cd_3[O(OH)]_2$ of two types, and cadmium hydroxide $Cd(OH)_2$. The silica, being amorphous, contributed no significant X-ray diffraction pattern.

Approximately 2.62 grams of the prepared silver-cadmium catalyst was charged to a 0.925 cm i.d. by 28 cm reactor tube. Hydrogen gas at 200 psig was passed over the catalyst in the reactor tube at 500 SCCM and the temperature was increased from 21° to 175° C over the course of one hour, at which time the gas was changed to one containing 1 part acrolein and 40 parts hydrogen. The reactor effluent was sampled using a gas sampling valve and gas chromatography. Table I summarizes the process conditions employed and the product yields obtained.

Powder X-ray diffraction examination of the used catalyst disclosed lines at 2.38, 2.06, 1.46 and 1.25 A, which indicated that a silver-cadmium alloy of the α-type was present on the silica. Chemical analysis of the alloy determined the content as 61.4% Ag and 38.5% Cd by weight. No discrete Ag or Cd crystallites were detectable.

TABLE I

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.2 | 125 | 206 | 7.25 | 2.90 | 73.80 | 26.2 | 0.0 |
| 2.3 | 175 | 198 | 6.97 | 41.42 | 76.20 | 22.0 | 1.8 |
| 0.9 | 175 | 500 | 17.60 | 97.40 | 76.80 | 11.2 | 12.0 |

EXAMPLE II

A silver-cadmium solution was prepared by dissolving 34 grams $AgNO_3$ (0.020 mole) and 30 grams $Cd(NO_3)_2.4H_2O$ (0.097 mole) in doubly distilled water to a total solution volume of 200 milliliters. A sodium hydroxide solution was perpared by dissolving 11.9 grams of NaOH (0.298 mole) in sufficient doubly distilled water to adjust the volume to 200 milliliters. Both solutions were then added dropwise with rapid stirring to 400 milliliters of distilled water. The resultant brown precipitate was recovered and added to a suspension of 100 milliliters of Cab-O-Sil M-5 in 200 milliliters of distilled water with rapid stirring. The suspension was filtered, and the filter cake was washed with 2 liters of distilled water. The moist filter cake was then calcined in air at 250° C for 20 hours. The material was cooled in a vacuum desiccator, and the crushed and screened to yield a 50-80 mesh fraction which by bulk chemical analysis was found to contain 61% Ag, 26% Cd and 12% $SiO_2$. Powder X-ray diffraction examination indicated that the silver was present as metallic crystallites and the cadmium was present as CdO.

A quantity of about 7.63 grams of this catalyst precursor was placed in a 0.925 cm i.d. by 28 cm reactor tube and 200 psig hydrogen flowing at 750 SCCM was passed over the catalyst precursor as the temperature was raised from 23° to 130° C over a period of 36 minutes, at the end of which time the gas was changed to one containing approximately 1 part acrolein to 40 parts hydrogen. Table II summarizes the results obtained under a variety of process conditions with this catalyst. X-ray diffraction analysis of the used catalyst exhibited strong sharp lines at 2.39, 2.07, 1.46, and 1.25 A with a strong, relatively sharp, back reflection. This indicated an α-phase silver-cadmium alloy on the silica with a composition of 70% Ag and 30% Cd by weight. No discrete silver or cadmium crystallites could be detected by bulk chemical analysis.

crystallites of two types, and 33% by weight of silica, with less than 0.05% K or Cl.

This material was crushed and screened to yield a 50-80 mesh fraction, 3.16 grams of which were loaded into 0.925 cm i.d. by 28 cm reactor tube. Hydrogen gas at 200 psig was passed over the catalyst at 750 SCCM and the temperature brought rapidly from 22° to 127° C; then the gas was changed to 1 part acrolein in approximately 40 parts hydrogen.

Table III summarizes the results obtained under various conditions employing this catalyst. The reactor effluent stream was analyzed by gas chromatographic techniques. Table III summarises the reactor conditions, and the analysis of liquid products trapped at −78° C in a collection vessel down stream from the reactor. Bulk chemical analysis of the used catalyst in conjunction with X-ray diffraction scanning indicated that a 62.9% silver and 37.1% cadmium alloy phase was present. Broad X-ray diffraction lines at 2.36, 2.05, 1.45, and 1.23 A along with broad back reflection lines were observed. No discrete silver or cadmium metallic crystallites were detected.

TABLE III

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.1 | 125 | 209 | 7.8 | 38.5 | 68.0 | 31.0 | 0.0 |
| 2.0 | 150 | 223 | 8.3 | 84.7 | 69.5 | 28.0 | 2.0 |
| TABLE IIIA | | | | | | | |
| 2.2 | 150 | 206 | 7.7 | 78.0 | 69.0 | 28.0 | 3.0 |
| 1.6 | 170 | 290 | 5.2 | 99.9 | 66.0 | 24.0 | 10.0 |
| 0.9 | 156 | 485 | 9.7 | 97.0 | 71.0 | 19.0 | 9.0 |
| 0.9 | 160 | 515 | 10.3 | 99.9 | 70.0 | 13.0 | 17.0 |

TABLE II

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.1 | 125 | 210 | 9.4 | 12.7 | 46.5 | 49.5 | 4.0 |
| 2.1 | 150 | 214 | 9.6 | 21.2 | 66.2 | 31.5 | 2.3 |
| 2.2 | 175 | 204 | 9.1 | 38.5 | 66.1 | 30.8 | 3.1 |
| 2.2 | 210 | 207 | 5.1 | ≈100 | 70.3 | 0.37 | 29.3 |

EXAMPLE III

For the preparation of a silver-cadmium solution, 34.7 grams $AgNO_3$ (0.204 mole) and 80.0 grams Cd $(NO_3)_2.4H_2O$ (0.259 mole) were dissolved in 100 milliliters of distilled water. To this solution was added 17.0 grams of 86.7% KOH (0.263 mole) dissolved in 50 milliliters of distilled water, followed by addition of 400 milliliters of distilled water. The slurry mixture which formed was added to 400 milliliters of Cab-O-Sil M-5 suspended in one liter of distilled water with rapid stirring. The resultant solids were filtered off, partially air dried overnight, and calcined in air at 250° C for 16 hours. After cooling in a vacuum desiccator, the material was partially crushed and extracted with distilled water for about 24 hours, then recalcined at 250° to 300° C for 21 hours in air. The resultant material contained 34% by weight silver, present as metallic crystallites, 17.9% by weight cadmium, as cadmium hydroxide

EXAMPLE IV

A solution was prepared by dissolving 13.07 grams $AgNO_3$ (0.077 mole) and 37.97 grams Cd $(NO_3)_2.4H_2O$ (0.123 mole) in 100 milliliters of distilled water. A second solution was prepared by dissolving 20.75 grams of KOH in distilled water. Both solutions were then rapidly and simultaneously added to a vigorously stirred 100 milliliters of distilled water, and the resulting precipitate was further suspended by the addition of 500 milliliters of distilled water. After 1 hour of stirring, 1000 milliliters of Cab-O-Sil M-5 were added, in addition to sufficient water at intervals to maintain mixture fluidity. The final volume was increased to 1800 milliliters. The pH of the supernatant phase was 6.5. Vacuum filtration was employed to product a filter cake, which was washed with 2000 milliliters of distilled water. The filter cake was calcined in air at 250° C for 25 hours. After cooling in a vacuum desiccator, the catalyst precursor was crushed and screened to yield a 50-80 mesh fraction. Bulk chemical analysis indicated that the catalyst contained 63.7% $SiO_2$, 7.9% Ag, 18.6% Cd and 0.4% K by weight. Powder X-ray diffraction study revealed strong lines due to CdO, and weak lines due to Ag.

About 2.5 grams of this material were charged to a 0.55 cm i.d. by 28 cm reactor tube. Under 197 psig hydrogen flowing at 750 SCCM the temperature was raised from 24° to 125° C over the course of 1.1 hours, at which time 1 part acrolein in 40 parts hydrogen replaced the pure hydrogen. Table IV lists the reactor conditions and the analysis of the liquid products collected in a trap held at −78° C under the reactor pressure.

X-ray diffraction analysis of the used catalyst indicated the presence of α-phase AgCd and γ-phase AgCd alloys. No discrete metallic cadmium or silver was observed. Lines were observed at 2.41, 2.36, 2.08, A, and a sharp line characteristic of γ at 1.67. The back reflection was weak. Bulk chemical analysis indicated that these alloys had an average composition of 29.8% Ag and 70.2% Cd.

A 7.35 grams quantity of this catalyst precursor were placed in a 0.925 cm i.d. by 28 cm reactor tube. Under 499 psig hydrogen flowing at 1500 SCCM, the reactor was heated to 200° from 18° C, maintained at 200° C for 15 minutes, and cooled to 125° C over a total period of one hour. The hydrogen was then replaced by 1 part acrolein in 111 parts hydrogen. Table V summarizes the results based on the analysis of liquid products collected at −78° C under reactor pressure.

A 2.71 gram quantity of the catalyst precursor was placed in a 0.55 cm i.d. by 28 cm reactor tube, and under 620 psig hydrogen flowing at 1500 SCCM the material was heated from 10° to 200° C over a period of one hour. The catalyst was maintained at 200° C for 15 minutes and then cooled rapidly to 125° C, at which time an acrolein/hydrogen stream replaced the pure hydrogen. Table V summarizes various reactor conditions and the composition of the liquid products collected in a trap held at −78° C and reactor pressure.

TABLE IV

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.30 | 125 | 197 | 6.1 | 12 | 73 | 21 | 1 |
| 2.30 | 150 | 198 | 6.1 | 14 | 74 | 26 | 0 |
| 2.20 | 175 | 201 | 6.2 | 8 | 74 | 26 | 0 |
| 0.89 | 125 | 505 | 7.8 | 7 | 77 | 23 | 0 |
| 0.89 | 150 | 506 | 7.8 | 11 | 77 | 22 | 0 |
| 0.88 | 175 | 512 | 7.9 | 33 | 77 | 17 | 2 |
| 0.87 | 185 | 516 | 8.0 | 54 | 73 | 21 | 3 |

EXAMPLE V

A solution of 34.1 grams AgNO$_3$ (0.20 mole) and 60.2 grams Cd(NO$_3$)$_2$.2H$_2$O (0.195 mole) in 200 milliliters of water was added simultaneously with a solution of 34.95 grams of 87.4% analytical reagent grade KOH X-ray diffraction analysis of the used catalyst indicated that the principal AgCd alloy was the α-phase with some γ-phase also present. Bulk chemical analysis indicated that the average composition of the silver cadmium alloy on silica was 58.2% Ag and 41.8% Cd.

TABLE V

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.90 | 125 | 502 | 18.7 | 61.0 | 72 | 15 | 11 |
| 0.89 | 150 | 504 | 18.8 | 82.0 | 76 | 14 | 8 |
| 0.89 | 175 | 501 | 18.7 | 99.4 | 66 | 3 | 31 |
| 0.90 | 180 | 502 | 18.7 | 99.7 | 68 | 1 | 31 |
| TABLE V-A | | | | | | | |
| 3.00 | 150 | 999 | 6.7 | 11.1 | 78.9[1] | 21.1 | 0.0 |
| 3.00 | 175 | 999 | 6.7 | 91.3 | 74.2[2] | 15.5 | 10.3 |

STY (Grams Allyl Alcohol/Liter Hour)
[1] 103
[2] 958

(0.591 mole) in 200 milliliters of water to 400 milliliters of rapidly stirred distilled water. The pH of the supernatant phase after addition was 6.0. The volume of the suspension was increased to 1500 milliliters, and 1000 milliliters of Cab-O-Sil M-5 were added with vigorous stirring. The total volume was adjusted to 2000 milliliters and the slurry was filtered. The filter cake was washed with 3000 milliliters of distilled water, calcined in air at 250° C for 215 hours, and the resulting catalyst precursor was crushed and screened to yield a 50–80 mesh fraction. Chemical analysis indicated that the composition contained 49.6% SiO$_2$, 25.9% Ag, 18.6% Cd, and 0.4% K. Powder X-ray diffraction indicated that metallic silver and cadmium oxide, CdO, both of medium order were present at this stage, besides the amorphous SiO$_2$ which did not contribute detectable X-ray diffraction lines.

EXAMPLE VI

A 28.77 gram quantity of analytical reagent grade KOH (0.446 mole) was added to 200 milliliters of distilled water, and the resultant solution was warmed to 100° C. With rapid stirring a solution of 25.26 grams AgNO$_3$ (0.149 mole) and 45.85 grams Cd(NO$_3$)$_2$.4H$_2$O (0.149 mole) in 100 milliliters of distilled water was added. The suspension was cooled and diluted by the addition of 1000 milliliters of 2° C distilled water followed by 100 milliliters of Cab-O-Sil M-5. Additional distilled water was added to adjust the total volume to 1800 milliliters. The pH of the supernatant phase was 6.5.

The suspension was vacuum filtered, and the filter cake was washed with 2000 milliliters of distilled water and calcined in air at 250° C for 20 hours. The catalyst precursor was then crushed and screened to provide a 50–80 mesh fraction. X-ray diffraction examination revealed principally CdO of medium order, and no detectable silver lines.

A 4.04 gram quantity of this material was placed in a 0.55 cm i.d. by 28 cm reactor tube. The reactor under 490 psig hydrogen flowing at 1500 SCCM was heated from 20° to 200° C, held at 200° C for 15 minutes and cooled to 125° C over the course of 1.6 hours. At this time, the hydrogen was replaced by 1 part acrolein in 109 parts hydrogen. Table VI summarizes various reactor conditions, and the resultant composition of liquid products collected in a trap held at −78° C and reactor pressure. The used catalyst, 5.7% silica with 65.7% alloys, consisted of well ordered $\alpha,\gamma$ and some $\epsilon$-phase AcCd alloy on $SiO_2$. The average alloy composition was 52.4% Ag and 46.6% Cd.

resultant composition of the liquid products collected in a trap held at −78° C and reactor pressure.

The used catalyst had a nitrogen BET surface area of 9.6 m²/grams, and contained primarily $\gamma AgCd$, with $\alpha$ and some $\epsilon$ AgCd alloy, all on silica. The average composition of the AgCd alloys was 54.9% Ag and 45.1% Cd.

TABLE VII

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.87 | 125 | 515 | 20.0 | 19.1 | 77.0[1] | 12.5 | 1.6 |
| 0.87 | 150 | 515 | 20.0 | 69.7 | 79.7[2] | 10.0 | 4.1 |
| 0.88 | 175 | 510 | 19.9 | 99.2 | 68.5[3] | 0.8 | 27.3 |

STY (Grams Allyl Alcohol/Liter Hour)
[1]13.3
[2]47.0
[3]84.9

TABLE VI

| Mole Percent Acrolein In Feed | catalyst Temp. °C | Reactor Pressue psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.91 | 125 | 494 | 7.9 | 3.95 | 69.2 | 18.0 | 4.4 |
| 0.89 | 150 | 503 | 8.1 | 10.80 | 77.7 | 19.3 | 1.0 |
| 0.89 | 175 | 506 | 8.1 | 55.00 | 78.7 | 12.8 | 9.8 |
| 0.89 | 190 | 506 | 8.1 | 97.60 | 70.9 | 5.1 | 23.1 |
| 0.91 | 200 | 496 | 7.9 | 99.10 | 61.2 | 2.7 | 35.7 |

EXAMPLE VII

To a solution of silver and cadmium nitrates containing 102 grams $AgNO_3$ (0.600 mole) and 138.9 $Cd(NO_3)_2 \cdot 2H_2O$ (0.450 mole) in 150 milliliters of distilled water, a solution of 60.9 grams of 98.6% analytical reagent grade NaOH in 150 milliliters of distilled water was added with rapid stirring. The resultant black gel turned light brown on suspending in an additional 1500 milliliters of doubly distilled water. The precipitate was separated from the solution by vacuum filtration, washed with 2000 milliliters of doubly distilled water, and then ground in a mortar and pestle with 150 milliliters of DuPont Ludox AS Colloidal Silica. The mixture was dried for 20 hours at 95° C, and calcined in air at 200° for 60 hours. The mixture was then crushed and screened to yield a 50–80 mesh fraction. The composition contained 18.8% $SiO_2$, 27.2% Ag and 30.6% Cd.

A 13.10 grams quantity of this material was placed in a 0.925 cm i.d. by 28 cm reactor tube. Under 100 psig gas (99% He, 1% $H_2$) flowing at 200 SCCM, the temperature was raised is 12 minutes to 75° C, then at 25° C per hour to 250° C and maintained at the final temperature for 65 hours. The catalyst was cooled to 125° C, and the gas stream was changed to 510 psig hydrogen flowing at 1500 SCCM. After 24 minutes, the gas was changed to 1 part acrolein in 113 parts hydrogen. Table VII summarizes various reactor conditions and the

EXAMPLE VIII

This Example illustrates the low conversions and low yields obtained when a silver-cadmium catalyst not in accordance with the present invention contains unalloyed silver crystallites.

A solution of 34 grams $AgNO_3$ (0.200 mole) and 30 grams $Cd(NO_3)_2 \cdot 4H_2O$ (0.097 mole) in 100 milliliters of distilled water was added with rapid stirring to 15.6 grams $NH_4HCO_3$ (0.197 mole) in 150 milliliters of distilled water. Carbon dioxide evolved and a yellow precipitate formed. With vigorous stirring to keep the precipitate in suspension, 200 milliliters of Cab-O-Sil M-5 was added and the resultant suspension stirred gently for 2 hours and allowed to settle overnight. The solids were filtered and washed with 500 milliliters of 4° C distilled water. The filter cake was dried and crushed and screened to yield a 50–80 mesh fraction. Bulk chemical analysis and powder X-ray diffraction analysis indicated that the catalyst precursor consisted of 48.9% Ag as Ag crystallites, 28.0% Cd as CdO, and 20.4% $SiO_2$ by weight.

A 2.97 gram quantity of the 50–80 mesh fraction was placed in a 0.925 cm i.d. by 28 cm reactor tube, and 203 psig hydrogen flowing at 750 SCCM was passed over the catalyst as the temperature was increased from 24° to 125° C over a period of 24 minutes. One part acrolein in 40 parts hydrogen was then substituted for the pure hydrogen gas. Table VIII summarizes the results obtained by gas chromatographic analysis of the reactor effluent stream.

The used catalyst, which analyzed as 30.9% Ag, 17.4% Cd and 29.7% $SiO_2$, was found by X-ray diffraction studies to have an AgCd phase containing $\alpha$-AgCd and $\gamma$-AgCd, and large pure Ag crystallites which indicated that a significant portion of the silver was not alloyed. The X-ray diffraction lines were at 2.40, 2.36, 2.04, 1.46-7, 1.44, 1.25, and 1.23. The Ag lines and back reflection indicated the presence of large Ag Crystals. The AgCd associated lines and back reflection were shaped.

The average composition of this alloy was 2% silver and 98% cadmium by chemical analysis. The used catalyst had a nitrogen BET surface area of 71.4 m²/gram.

TABLE VIII

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.2 | 125 | 201 | 8.1 | 20.3 | 27.5 | 67.1 | 5.4 |
| 2.2 | 150 | 203 | 8.2 | 27.7 | 34.1 | 62.1 | 3.8 |
| 2.2 | 175 | 206 | 8.3 | 23.4 | 32.8 | 62.8 | 4.3 |
| 0.9 | 175 | 494 | 10.7 | 49.5 | 0.0 | 87.8 | 12.2 |

TABLE IX

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.90 | 125 | 499 | 21.0 | 3 | 12 | 5 | 54 |
| 0.88 | 150 | 511 | 21.5 | 2 | 4 | 5 | 55 |
| 0.92 | 190 | 490 | 20.6 | 16 | 28 | 4 | 3 |
| 0.92 | 225 | 491 | 20.7 | 33 | 33 | 7 | 2 |
| 0.90 | 250 | 498 | 20.8 | 56 | 27 | 13 | 1 |

EXAMPLE IX

This Example illustrates the low conversions and low yields obtained when a silver-cadmium catalyst not in accordance with the present invention contains a minor quantity of silver metal and consists substantially of cadmium metal on a carrier substrate.

Two solutions were prepared by dissolving 1.01 grams $AgNO_3$ (0.006 mole) and 89.91 grams $Cd(NO_3)_2 \cdot 4H_2O$ (0.291 mole) in 100 distilled water, and dissolving 37.81 grams 87.4% reagent grade KOH (0.589 mole) in 100 milliliters of distilled water. Both solutions were added rapidly and simultaneously to 200 milliliters of vigorously stirred distilled water. The pH of the liquid medium was about 6.5. About 500 milliliters of Cab-O-Sil M-5 were added along with sufficient water to keep the medium fluid. The volume was adjusted to 1800 milliliters with additional distilled water.

A filter cake was recovered by vacuum filtration, washed with 2000 milliliters of distilled water, and then calcined in air at 250° C for 17.5 hours. The reddish tan catalyst precursor was cooled to room temperature in a vacuum desiccator prior to being crushed and screened to provide a 50-80 mesh fraction. Chemical analysis indicated that the composition contained 32% $SiO_2$, 51% Cd, and 1% Ag. CdO of medium order was the Cd species found by X-ray diffraction.

A 8.15 gram quantity of this material were placed in a 0.925 cm i.d. by 28 cm reactor tube. The material was heated under 499 psig hydrogen flowing at 1400 SCCM from 18° to 200° C, maintained at 200° C for 15 minutes, and cooled to 125° C over a total period of 1.6 hours. 1 part acrolein in 40 parts hydrogen was intorduced 12 minutes later.

Table IX summarizes various reactor conditions and the resultant composition of the liquid products collected in a trap at −78° C and reactor pressure.

The used catalyst, by X-ray diffraction, appeared to have well ordered cadmium rich η-phase AgCd with a structure not differing significantly from metallic Cd.

EXAMPLE X

This Example illustrates the low conversions and low yields obtained when a silver-cadmium catalyst not in accordance with the present invention contains a minor quantity of cadmium metal and consists substantially of silver metal on a carrier substrate.

To a solution of silver and cadmium nitrates prepared by adding 102 grams $AgNO_3$ (0.600 mole) and 90 grams $Cd(NO_3)_2 \cdot 4H_2O$ (0.292 mole) to 120 milliliters of distilled water, 120 milliliters of 1 normal sodium hydroxide solution was added with rapid stirring. The resultant precipitate was separated from the solution by vacuum filtration, washed with 600 milliliters of distilled water, and resuspended in 90 milliliters of DuPont Ludox AS Colloidal Silica with rapid stirring. The suspension was air dried at 100° C for 17 hours, and calcined at 250° C for 20 hours in air. The catalyst precursor was cooled in a vacuum desiccator, and then crushed and screened to yield a 50–80 mesh fraction. By chemical analysis it was determined that the composition contained 45.4% silica, 27.9% silver, 1% cadmium and 2.8% sodium. Well ordered crystals of CdO, $Cd(OH)_2$ and Ag were present.

A 3.96 gram quantity of this material was placed in a 0.55 cm i.d. by 28 cm reactor tube. Under 494 psig hydrogen flowing at 1300 SCCM the reactor was rapidly heated from 18° to 250° C, held at 250° C for 30 minutes, and then cooled to 125° C. After an additional six minutes, 1 part acrolein in 110 parts hydrogen was introduced. Table X summarizes reactor conditions and the resultant composition of the products collected in a trap held at −78° C and reactor pressure. The used catalyst had a nitrogen surface area of 81.5 m²/gram, and powder X-ray diffraction examination identified well ordered silver crystals on silica. The used catalyst had a 96.5% silver and 3.5% cadmium metal alloy content.

TABLE X

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.92 | 75 | 489 | 5.5 | 19.2 | 45.9 | 51.8 | 1.0 |
| 0.92 | 100 | 490 | 5.5 | 46.7 | 49.9 | 47.6 | 1.0 |
| 0.91 | 125 | 495 | 5.5 | 99.4 | 44.4 | 32.1 | 23.1 |

EXAMPLE XI

This Example illustrates the lower conversions obtained when a silver-cadmium catalyst not in accordance with the present invention contains coprecipitated silver-cadmium alloy without a carrier substrate.

Two solutions were prepared by dissolving 34.0 grams $AgNO_3$ (0.200 mole) and 41.2 grams $Cd(NO_3)_2 \cdot 4H_2O$ (0.134 mole) in 100 milliliters of distilled water, and 30.12 grams of 87.0% analytical reagent grade KOH (0.537 mole) in 100 milliliters of distilled water. Both solutions were added simultaneously and in a rapid dropwise fashion to 400 milliliters of vigorously stirred distilled water. The pH was adjusted to 7.0 with KOH or $HNO_3$ as needed, and the volume was increased with distilled water to 2000 milliliters. The suspension was allowed to settle at 4° C, protected from light. The clear supernatant liquid was drawn off and fresh distilled water was added to adjust the volume to 2000 milliliters.

The solids were recovered from the solution by vacuum filtration, washed with 2000 milliliters of distilled water, and calcined in air at 200° C for 20 hours. After cooling in a vacuum desiccator, the material was crushed and sieved to yield a 50-80 mesh fraction. Chemical analysis indicated that the bulk material was 55.6% Ag and 43.4% Cd.

A 6.83 gram quantity of this material was placed in a 0.55 cm i.d. by 28 cm reactor tube. Over a period of two hours, the catalyst was treated with 501 psig hydrogen flowing at 1500 SCCM heated from 24° to 250° C, held at 250° C for 15 minutes, and cooled to 125° C. At this time, 1 part acrolein in 111 parts hydrogen replaced the pure hydrogen flow stream.

Table XI summarizes various reactor conditions and the resultant composition of the liquid products collected in a trap held at −78° C and reactor pressure. The used catalyst had a nitrogen BET surface area of 0.15 m²/gram.

$NO_3)_2 \cdot 3H_2O$ (0.00248 mole) in 100 milliliters of distilled water, and 25.70 grams of 87.4% analytical reagent grade KOH (0.4003 mole) in 100 milliliters of distilled water. Both solutions were added rapidly and simultaneously to 100 milliliters of vigorously stirred distilled water. After the formation of the blackish gelatinous precipitate, the volume of the system was adjusted to 1000 milliliters with additional distilled water. The pH of the supernatant was 6.5. 1000 milliliters of Cab-O-Sil M-5 and sufficient water to adjust the total volume to 1800 milliliters were added. The precipitate was removed from the supernatant solution by vacuum filtration and washed with 2000 milliliters of distilled water. The solid was then calcined in air at 250° C for 20 hours. The material was crushed and sieved to yield a 50-80 mesh fraction. The composition analyzed as containing 53.7% $SiO_2$, 26.9% Ag, 16.9% Cd, 0.5% K, and 0.8% Cu. Powder X-ray diffraction examination identified only lines indicating CdO.

A 7.72 grams quantity of this material was placed in a 0.925 cm i.d. by 29 cm reactor tube. With 500 psig hydrogen flowing over the catalyst precusor at 1500 SCCM, the temperature of the reactor was increased from 19° to 200° C, held at 200° C for 15 minutes, and cooled to 125° C. The hydrogen stream was replaced with 1 part acrolein in 110 parts hydrogen.

Table XII summarizes various reactor conditions and the resultant composition of liquid products collected in a trap held at −78° C and reactor pressure. The used catalyst had a surface area of 47.8 m²/gm, and exhibited a silver rich α-phase AgCd(CU) alloy on silica with an average composition of 60.31% Ag, 37.89% Cd and 1.79% Cu.

In the same manner, a second catalyst was prepared with a bulk content of 54.4% $SiO_2$, 31.6% Ag, 14.1% Cd, and about 660 ppm Cu.

Table XIIA summarizes various reactor conditions and the resultant composition of the liquid products collected in a trap held at −78%C and reactor pressure employing the second catalyst.

The used catalyst, on powder X-ray diffraction examination, exhibited sharp lines at 2.36, 2.04, 1.44, 1.23 A, with a strong sharp back reflection pattern evident. Chemical analysis indicated a silver rich α-phase AgCd-(Cu) alloy of 69.0% Ag, 30.8% Cd, and 0.14% Cu average composition on the silica.

TABLE XI

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.89 | 125 | 503 | 5.6 | 1.4 | 33.9 | 47.4 | 0.0 |
| 0.88 | 150 | 508 | 5.6 | 1.5 | 30.3 | 53.9 | 0.0 |
| 0.86 | 175 | 523 | 5.9 | 7.0 | 73.2 | 25.2 | 0.6 |
| 0.86 | 185 | 522 | 5.9 | 17.7 | 74.5 | 19.5 | 1.5 |
| 0.86 | 200 | 524 | 5.9 | 27.3 | 69.8 | 22.5 | 2.6 |

EXAMPLE XII

This Example illustrates the conversions and yields obtained when a silver-cadmium alloy catalyst contains copper metal.

Two solutions were prepared by dissolving 34.00 grams $AgNO_3$ (0.20015 mole), 30.00 grams $Cd(NO_3)_2 \cdot 4H_2O$ (0.09725 mole), and 0.60 gram Cu(-

TABLE XII

| Mole Percent Acrolein In Feed | Catalyst Temp. °C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.89 | 125 | 507 | 14.2 | 44.3 | 68.1 | 23.9 | 2.8 |
| 0.89 | 150 | 508 | 14.2 | 90.9 | 66.3 | 23.9 | 9.4 |
| 0.89 | 175 | 510 | 14.3 | 99.6 | 57.7 | 6.7 | 35.5 |
| TABLE XII-A | | | | | | | |
| 0.88 | 125 | 510 | 9.0 | 18.0 | 82.6 | 15.2 | 2.2 |
| 0.88 | 150 | 510 | 9.0 | 30.3 | 74.8 | 15.6 | 1.4 |
| 0.88 | 175 | 510 | 9.0 | 63.8 | 77.2 | 19.4 | 3.4 |

What is claimed is:

1. An improved hydrogenation process for converting a $\alpha,\beta$-olefinically unsaturated carbonylic compound into the corresponding allylic alcohol derivative which comprises reacting an $\alpha,\beta$-olefinically unsaturated carbonylic compound with hydrogen in the vapor phase at a temperature between about 0° and 300° C and a pressure between about 15 and 15,000 psi in the presence of a catalyst comprising a silver-cadmium alloy on a carrier substrate, wherein the atomic ratio of silver to cadmium in the alloy is in the range of between about 0.1 and 3 to 1, and the alloy exhibits an X-ray diffraction pattern which is substantially free of detectable unalloyed metal crystallite lines.

2. A process in accordance with claim 1 wherein the carbonylic compound is acrolein.

3. A process in accordance with claim 1 wherein the carbonylic compound is methacrolein.

4. A process in accordance with claim 1 wherein the carbonylic compound is crotonaldehyde.

5. A process in accordance with claim 1 wherein the carbonylic compound is methylvinyl ketone.

6. A process in accordance with claim 1 wherein the carbonylic compound is methylisopropenyl ketone.

7. A process in accordance with claim 1 wherein the silver-cadmium alloy consists of more than about 50 percent $\gamma$-phase silver-cadmium crystallites.

8. A process in accordance with claim 1 wherein the silver-cadmium alloy consists of more than 50 percent $\alpha$-phase silver-cadmium crystallites, and the X-ray diffraction pattern of the $\alpha$-phase silver-cadmium alloy does not exhibit line splitting.

9. A process in accordance with claim 1 wherein the silver-cadmium alloy consists essentially of $\alpha$-phase and $\gamma$-phase silver-cadmium crystallites, and the X-ray diffraction pattern of the $\alpha$-phase silver-cadmium alloy does not exhibit line splitting.

10. A process in accordance with claim 1 wherein the silver cadmium alloy consists essentially of $\alpha$-phase, $\gamma$-phase, and $\epsilon$-phase silver cadmium alloy crystallites, and the X-ray diffraction pattern of the $\alpha$-phase silver cadmium alloy does not exhibit line splitting.

* * * * *